(12) United States Patent
Lee et al.

(10) Patent No.: US 8,361,790 B2
(45) Date of Patent: Jan. 29, 2013

(54) HUMAN HOST CELL FOR PRODUCING RECOMBINANT PROTEINS WITH HIGH QUALITY AND QUANTITY

(75) Inventors: HyunJoo Lee, Incheon (KR); JongMook Kim, Incheon (KR); MinSeok Chang, Incheon (KR)

(73) Assignee: Celltrion, Inc. (KR)

( * ) Notice: Subject to any disclaimer, the term of this patent is extended or adjusted under 35 U.S.C. 154(b) by 0 days.

(21) Appl. No.: 12/937,499

(22) PCT Filed: Apr. 10, 2009

(86) PCT No.: PCT/KR2009/001856
§ 371 (c)(1),
(2), (4) Date: Oct. 12, 2010

(87) PCT Pub. No.: WO2009/125999
PCT Pub. Date: Oct. 15, 2009

(65) Prior Publication Data
US 2011/0065184 A1 Mar. 17, 2011

(30) Foreign Application Priority Data
Apr. 12, 2008 (KR) ........................ 10-2008-0033972

(51) Int. Cl.
C12N 5/02 (2006.01)
C12N 5/06 (2006.01)
(52) U.S. Cl. ......... 435/325; 435/326; 435/335; 435/346
(58) Field of Classification Search ........................ None
See application file for complete search history.

(56) References Cited

U.S. PATENT DOCUMENTS 6,136,599 A * 10/2000 Cho .............................. 435/325

FOREIGN PATENT DOCUMENTS

| JP | 1989-060373 A | 3/1989 |
|---|---|---|
| KR | 10-1986-0000897 | 9/1983 |
| KR | 1020020002360 | 1/2002 |
| KR | 1020020013481 | 2/2002 |

OTHER PUBLICATIONS

National Center for Infectious Diseases, Epstein-Barr Virus and Infectious Mononucleosis. May 16, 2006, p. 1-4.*
ATCC Cell Biology Catalogue 2007. Copyright 2006. American Type Culture Collection, pp. 1-16 and 164.*
International Search Report—PCT/KR2009/001856 dated Nov. 20, 2009.
Written Opinion—PCT/KR2009/001856 dated Nov. 20, 2009.
M.S, Cho, et al., "Versatile Expression system for rapid and stable production of recombinant proteins", 2003, Biotech. Prog 19:229-232.
Frits J. Fallaux, et al., "New helper cells and matched early region 1-deleted adenovirus vectors prevent generation of replication-competent adenoviruses", 1998, Human Gene Therapy, 9:1909-1917.
David Jones, et al., "High level expression of recombinant IgG in the Human cell line PER.C6.", 2003, Biotechnol. Prog. 19:163-168.
Liangzhi Xie, et al., "Large-Scale propagation of a replication-defective adenovirus vector in stirred-tank bioreactor PER.C6 cell culture under sparging conditions", 2003, Biotech. Bioeng. 83:45-52.
M.S. Cho, H. Yee, S. Chan, "Establishment of a human somatic hybrid cell line for recombinant protein production", 2002, J Biomedical Science 9:631-638.
Cornelia M. Gorman, et al., "Expression of recombinant plasmids in mammalian cells in enhanced by sodium butyrate", 1983, Nucl Acid Res 11:7631-7648.
Pey-Jium Chang, et al., "Open reading frame 50 protein of Kaposi's sarcoma-Associated herpesvirus directly activates the viral PAN and K12 genes by binding to related response elements", 2002, J Virol. 76:3168-3178.
Matsuo, T. et al., "Persistence of the entire Epstein-Barr virus genome integrated into human lymphocyte DNA", Science, Dec. 14, 1984, 226:1322-1325.
Ann Henderson et al., "Chromosome site for Epstein-Barr virus DNA in a Burkitt tumor cell line and in lymphocytes growth-transformed in vitro", 1983, PNAS USA, 80:1987-1991.
Camille Rose, et al., "Detection of Epstein-Barr virus genomes in peripheral blood B cells from solid-organ transplant recipients by fluorescence in situ hybridization", Journal of Clinical Microbiology, 2002, 40:2533-2544.
G. Cabras, et al., "Epstein-Barr virus encoded BALF1 gene is transcribed in Burkitt's lymphoma cell lines and in nasopharyngeal carcinoma's biopsies", Journal of Clinical Virology, 2005, 34:26-34.
Jill Countryman et al., "Polymorphic proteins encoded within BZLFI of defective and standard Epstein-Barr viruses disrupt latency", 1987, J Virol, 61:3672-3679.
Jeffery Sample, et al., "Two related Epstein-Barr virus membrane proteins are encoded by separate genes", 1987, Journal of Virology, 63:933-937.
Michele Bernasconi, et al., "Quantitative profiling of housekeeping and Epstein-Barr virus gene transcription in Burkitt lymphoma cell lines using an oligonucleotide microarray", Virology Journal, 2006, 3:43-57.
Daniel Y. Lee, et al., "A positive role histone acetylation in transcription factor access to nucleosomal DNA", 1993, Cell 72:73-84.
M.I. Cockett, et al., "High level expression of tissue inhibitor of metalloproteinases in chinese hamster ovary cells using glutamine synthetase gene amplification", 1990, Bio/technology 8:662-667.
Kern Hee Chang, et al., "N-Acetylcysteine increases the biosynthesis of recombinant EPO in Apoptotic chinese hamster ovary cells", 1999, Free Rad Res 30:85-91.
William L. Marshall, et al., "Epstein-Barr virus encodes a novel homolog of the bcl-2 oncogene that inhibits apoptosis and associates with bax and bak", 1999, Journal of Virology. 73:5181-5185.
David S. Bellows, et al., "Epstein-Barr virus BALFI is a BCL-2-like antagonist of the herpesvirus antiapoptotic BCL-2 proteins", Journal of Virology, Mar. 2002, 76: 2469-2479.
Laurence Cuisset, et al., "A protein phosphatase is involved in the inhibition of histone deacetylation by sodium butyrate", Biochemical and Biophysical Research Communications, 246:760-764 (1998).
Japanese Office Action issued Dec. 4, 2012 for Application No. JP 2011-503913.

* cited by examiner

Primary Examiner — Jennifer Dunston
Assistant Examiner — Channing S Mahatan
(74) Attorney, Agent, or Firm — Cantor Colburn LLP

(57) ABSTRACT

The present invention relates to a human host cell generated from fusion of a human embryonic kidney-derived cell and a human B-cell-derived cell, by using genetic engineering techniques. The human host cell with stable characteristics well preserved may be efficiently used to produce heterologous desired recombinant protein-based pharmaceuticals.

5 Claims, 15 Drawing Sheets

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: first primer for GnTIII gene (sense)

<400> SEQUENCE: 1
gacgtggtgg acgcctttgt                                           20

<210> SEQ ID NO 2
<211> LENGTH: 20
<212> TYPE: DNA
<213> ORGANISM: Artificial Sequence
<220> FEATURE:
<223> OTHER INFORMATION: first primer for GnTIII gene (antisense)

<400> SEQUENCE: 2
cgaccactgc accaggatgt                                           20

<210> SEQ ID NO 3
<211> LENGTH: 25
<212> TYPE: DNA
<213> ORGANISM: Artificial Sequence
<220> FEATURE:
<223> OTHER INFORMATION: second primer for GnTIII gene (sense)

<400> SEQUENCE: 3

-continued caaggtgctc tatgtcttcc tggac                                    25

<210> SEQ ID NO 4
<211> LENGTH: 24
<212> TYPE: DNA
<213> ORGANISM: Artificial Sequence
<220> FEATURE:
<223> OTHER INFORMATION: second primer for GnTIII gene (antisense)

<400> SEQUENCE: 4
cggtcgtagt tcttcagcag gtac                                     24

<210> SEQ ID NO 5
<211> LENGTH: 22
<212> TYPE: DNA
<213> ORGANISM: Artificial Sequence
<220> FEATURE:
<223> OTHER INFORMATION: primer for Ig-mu gene (sense)

<400> SEQUENCE: 5
acaaggtgac cagcacactg ac                                       22

<210> SEQ ID NO 6
<211> LENGTH: 25
<212> TYPE: DNA
<213> ORGANISM: Artificial Sequence
<220> FEATURE:
<223> OTHER INFORMATION: primer for Ig-mu gene (antisense)

<400> SEQUENCE: 6
gtgacggtgg tactgtagaa gaggc                                    25

<210> SEQ ID NO 7
<211> LENGTH: 20
<212> TYPE: DNA
<213> ORGANISM: Artificial Sequence
<220> FEATURE:
<223> OTHER INFORMATION: first primer for EBNA1 gene (sense)

<400> SEQUENCE: 7
gtccaagttg cattggctgc                                          20

<210> SEQ ID NO 8
<211> LENGTH: 22
<212> TYPE: DNA
<213> ORGANISM: Artificial Sequence
<220> FEATURE:
<223> OTHER INFORMATION: first primer for EBNA1 gene (antisense)

<400> SEQUENCE: 8
ctcatctcca tcacctcctt ca                                       22

<210> SEQ ID NO 9
<211> LENGTH: 19
<212> TYPE: DNA
<213> ORGANISM: Artificial Sequence
<220> FEATURE:
<223> OTHER INFORMATION: second primer for EBNA1 gene (sense)

<400> SEQUENCE: 9
agaaggtgcc cagatggtg                                           19

<210> SEQ ID NO 10
<211> LENGTH: 22
<212> TYPE: DNA
<213> ORGANISM: Artificial Sequence

```
<220> FEATURE:
<223> OTHER INFORMATION: second primer for EBNA1 gene (antisense)

<400> SEQUENCE: 10
ctcatctcca tcacctcctt ca                                           22

<210> SEQ ID NO 11
<211> LENGTH: 25
<212> TYPE: DNA
<213> ORGANISM: Artificial Sequence
<220> FEATURE:
<223> OTHER INFORMATION: primer for BHRF1 gene (sense)

<400> SEQUENCE: 11
tacgcattag agaccactt gagcc                                         25

<210> SEQ ID NO 12
<211> LENGTH: 20
<212> TYPE: DNA
<213> ORGANISM: Artificial Sequence
<220> FEATURE:
<223> OTHER INFORMATION: primer for BHRF1 gene (antisense)

<400> SEQUENCE: 12
gtcaaggttt cgtctgtgtg                                              20

<210> SEQ ID NO 13
<211> LENGTH: 24
<212> TYPE: DNA
<213> ORGANISM: Artificial Sequence
<220> FEATURE:
<223> OTHER INFORMATION: primer for BALF1 gene (sense)

<400> SEQUENCE: 13
gaggccagcc aagtctacag attc                                         24

<210> SEQ ID NO 14
<211> LENGTH: 23
<212> TYPE: DNA
<213> ORGANISM: Artificial Sequence
<220> FEATURE:
<223> OTHER INFORMATION: primer for BALF1 gene (antisense)

<400> SEQUENCE: 14
gaactgacgt ctcagcgatc ttg                                          23
```

HUMAN HOST CELL FOR PRODUCING RECOMBINANT PROTEINS WITH HIGH QUALITY AND QUANTITY

TECHNICAL FIELD

The present invention relates to a human host cell for producing recombinant proteins with high quality and quantity, and more particularly, to a human host cell generated from fusion of a human embryonic kidney-derived cell and a human B-cell-derived cell, by using genetic engineering techniques, wherein the human host cell has stable desired characteristics well-preserved to be efficiently used for production of heterologous recombinant protein-based pharmaceuticals.

BACKGROUND ART

To date, most recombinant protein-based pharmaceuticals for human use have been produced using non-human mammalian cells, for example, Chinese hamster ovary (CHO) cells, mouse melanoma (NSO) cells, and mouse myeloma (SP2/0) cells. There have been attempts to use human cell lines for the production of therapeutic recombinant proteins, for example, the production of active protein C using human embryonic kidney 293 cells (Eli Lylly, 2001), the production of interferon-beta using Namalwa cells (Wellcome Research Laboratory, 1999), the production of truncated recombinant factor VIII and a variety of antibodies by HKB11 cells (Cho et al., 2003, Biotech. Prog 19:229-232), and the production of a variety of antibodies and virus DNA by PER.C6 cells (Fallaux et al., 1998, Human Gene Therapy, 9:1909-1917) (Jones et al., 2003, Biotechnol. Prog. 19:163-168 and Xie et al., 2003, Biotech. Bioeng. 83:45-52).

Korean Patent No. 627,753 discloses the use of human host cells, HKB11 cells to produce proteins which are difficult to express in CHO cells (Cho et al., 2003, Biotech. Prog 19:229-232) (Cho and Chan, 2002, Biomedical Science 9:631-638 and U.S. Pat. No. 6,136,599). Korean Patent No. 616,028 discloses a method of producing truncated recombinant factor VIII by HKB11 cells. The HKB cell is a cell line derived from HH514-16 and includes a genome of Epstein Barr virus (EBV) which is deficient in B-cell immobilization and virus production (Rabson et al., 1983, PNAS USA 87:3660-3664). The HKB cells show characteristics such as high-density growth, high transfection efficiency, and simple MTX-induced amplification, massive secretion of target proteins, and extinction of IgM expression, which are suitable for producing therapeutic proteins. However, it was found that EBV tended to be isolated from the HKB cell during the cultivation of the HKB cell (Chang et al., 2002, J. Virol. 76:3168-3178). This tendency indicates that the HKB cell may become devoid of EBV, thereby failing to preserve various beneficial properties for effective expression of heterologous genes. That is, the HKB cell loses EBV when cultured for a long period of time, so that therapeutic recombinant proteins may not be produced.

Since a EBV genome does not exist as episomes but is inserted into chromosomes in Namalwa cells (Matsuo et al., Science 14 Dec. 1984: 1322-1325, Henderson et al., 1983, PNAS USA 80: 1987-1991 and Rose et al., 2002, J. Clin. Microbiol. 40:2533-2544), the inventors have developed a novel human host cell line which retains EBV-derived features without virus production, using Namalwa cells.

DETAILED DESCRIPTION OF THE INVENTION

Technical Problem

An object of the present invention is to provide a human host cell generated from fusion of a human embryonic kidney-derived cell and a human B-cell-derived cell, with an Epstein-Barr virus (EBV) genome inserted into its chromosomes.

Another object of the present invention is to provide a use of the human host cell for producing recombinant proteins.

Technical Solution

According to an aspect of the present invention, there is provided a human host cell generated from fusion of a human embryonic kidney-derived cell and a human B-cell-derived cell, with an Epstein-Barr virus (EBV) genome inserted into its chromosomes.

According to another aspect of the present invention, there is provided a use of the human host cell for producing recombinant proteins including monoclonal antibodies.

The present invention will now be described more fully with reference to the accompanying drawings, in which exemplary embodiments of the invention are shown.

A human host cell according to an embodiment of the present invention is generated from fusion of a human embryonic kidney-derived cell and a human B-cell-derived cell, with an Epstein-Barr virus (EBV) genome inserted into its chromosomes.

The human embryonic kidney-derived cell may include a human embryonic kidney cell, a cell derived from a human embryonic kidney cell, a cell derived from another cell of human embryonic kidney origin, and a cell resulting from mitotic division of any of the cells mentioned above. Used herein, "derived from" is intended to include, but is not limited to, normal mitotic cell division and processes such as transfections, cell fusions, or other genetic engineering or cell biology techniques used to alter cells or produce cells with new characteristics. In particular, the human embryonic kidney-derived cell may be a 293 derived cell, and preferably, a 293 cell. The 293 cell exhibits high transfection efficiency and a high level of protein productivity but aggregation occurs in a serum-free suspension culture.

The human B-cell-derived cell with the EBV genome in its chromosomes, may include a human B-cell, a cell derived from a human B-cell, a cell derived from another human B-cell, or a cell resulting from mitotic division of the cells. Used herein, "derived from" is intended to include, but is not limited to, normal mitotic cell division, transfections, cell fusions, or other genetic engineering or cell biology techniques used to alter cells or produce cells with new characteristics. In particular, the human B-cell-derived cell with the EBV genome in its chromosomes may be a Namalwa cell. The Namalwa cell has low transfection efficiency but grows well in a suspension culture without aggregation.

The EBV genome generally exists as episomes in B-cells but is inserted into chromosomes of some B-cells such as Namalwa cells. Using these exceptional and unique features, an embodiment of the preset invention provides a stable human host cell, which does not produce a virus despite having information of the virus, may be prepared. Since an Epstein-Barr nuclear antigen 1 (EBNA1) gene required for an oriP expression vector and BHRF1 and BALF1 genes for anti-apoptosis (Cabras et al., 2005, J Clinical Virology 34:26-34) among the EBV genome genes are expressed in Namalwa cells, these genes are efficiently used as information of a virus in a host cell. In addition, since a BZLF1 gene (Countryman et al., 1987, J Virol, 61:3672-3679) inducing initial protein expression as a lytic cycle gene and a LMP2 gene (Sample et al., J Virol 63:933-937) expressed only in an episomal genome are not expressed in Namalwa cells, a safe host cell without virus production may be prepared (M. Bernasconi et al., Virology Journal, 2006, 3:43-57).

The human host cell according to the current embodiment is generated from fusion of the human embryonic kidney-derived cell and the human B-cell-derived cell with an Epstein-Barr virus (EBV) genome inserted into its chromosomes. Thus, the human host cell is a new cell line having beneficial properties of both the human embryonic kidney-derived cell, for example, the 293 cell, and the human B-cell-derived cell, for example, the Namalwa cell. By selecting the 293 cell as one fusion partner for the human host cell, the transfection efficiency and protein productivity of the human host cell may be improved. In addition, by selecting the Namalwa cell as the other fusion partner, suspension culture of the human host cell may be easily performed, the human host cell may be safely prepared without producing a virus, an EBNA1 gene is not required for the oriP expression vector since EBNA1 protein may be continuously expressed, and apoptosis may be inhibited by a viral bcl-2 homolog gene such as BHRF1 and BALF1.

Furthermore, the human B-cell-derived cell, for example, the Namalwa cell, may be a HAT-sensitive and G418-resistant cell. In order to prepare the human host cell according to the current embodiment which has useful properties of both the human embryonic kidney-derived cell and the human B-cell-derived cell, a process of selecting clones having the useful properties of both cells needs to be performed after the fusion of the cells. Since the human embryonic kidney-derived cell, i.e., the 293 cell, is HAT-resistant and G418-sensitive, the human B-cell-derived cell, for example the Namalwa cell, which is HAT-sensitive and G418-resistant is chosen as the fusion partner for the human embryonic kidney-derived cell.

According to an embodiment of the present invention, the 293 cell and the Namalwa cell are used to develop a new human host cell generated from the fusion of the human embryonic kidney-derived cell and the human B-cell-derived cell. First, a Namalwa cell line is cultured in a culture medium supplemented with fetal bovine serum (FBS) and 6-thioguanine in order to derive the Namalwa cell, which is HAT-sensitive and G418-resistant, as a partner for fusion with the 293 cell. Sensitivity of the Namalwa cell to a HAT-containing culture medium was measured while increasing the concentration of 6-thioguanine for a selection period of several months. A HAT-sensitive Namalwa cell population is transfected with pSV2neo plasmid, and cell population having resistance to G418 is selected to be used as a fusion partner of the 293 cell. Then, fusion of the 293 cell and the HAT-sensitive Namalwa cell is carried out according to a method of using polyethylene glycol (PEG) disclosed in Kennett RH. Cell fusion. Methods Enzymol 58:345-359; 1979. However, the cell fusion is not limited to the method and may be performed according to methods commonly used in the art.

The human host cell according to an embodiment of the present invention, generated from the fusion of the 293 cell and the Namalwa cell is designated Fusion of 293 and Namalwa (F2N) cell. It is expected that the EBV genome is not lost from the F2N cell during a long-term culture since the EBV genome exists inserted into chromosomes of the F2N, unlike HKB cells which have similar features to F2N cells. In order to prove this, several F2N clones are selected and cultured in a serum free suspension culture medium for longer than 1 year. As a result, the expression of EBNA1 is observed in all of the cell population cultured in the serum free suspension culture medium for longer than 1 year (See FIGS. 5 and 6), which demonstrates that the EBV genome is not lost from the F2N cell even though the F2N cell is cultured for a long period of time.

In order to select clones having high transfection efficiency in the F2N cell, the F2N cell is transfected with a pCT132 vector (See FIG. 3) expressing IgG, and the resultant is analyzed using an enzyme-linked immunosorbent assay (ELISA) to evaluate antibody production efficiency (See FIGS. 4A to 4C). In general, the transfection efficiency of the F2N cell is higher than that of the 293 cell. Furthermore, one of the clones which has a high transfection efficiency and grows well in the serum free suspension culture medium is selected and designated F2N78, and then deposited in the Korean Collection for Type Cultures (KCTC), Biological Resource Center, Korean Research Institute of Bioscience and Biotechnology, 111 Kwahack-ro, Yuseong-gu, Daejeon, on Apr. 11, 2008 (Accession number: KCTC11309BP).

In order to identify whether the F2N cell, which is generated from the fusion of the 293 cell and the Namalwa cell, has desired beneficial properties, a reverse transcription-polymerase chain reaction (RT-PCR) wass performed using mRNA extracted from the F2N78 cell to identify expressions of EBNA1, Ig-mu, Ig-kappa, and N-acetylglucosaminyl transferase III (GnTIII) of the F2N78 clone. The result showed that the F2N78 clone express EBNA1 and GnTIII but did not express IgM (See FIG. 6). In order to identify expressions of EBNA1, IgM, and α(2,6)sialyl transferase (α(2,6)ST), immunofluorescence (IF) was performed. The result showed that the F2N78 expressed EBNA1 and α(2,6)ST but did not express IgM (See FIG. 5). In this regard, the expression of EBNA1 indicates the presence of the EBV genome in the F2N clones, and the expressions of GnTIII and α(2,6)ST indicate glycosylation profiles similar to those of humans. The nonexpression of IgM indicates that the expression of immunoglobulin observed in the Namalwa cell is inhibited in the F2N cell derived from the cell fusion. These features are required to produce a therapeutic recombinant monoclonal antibody from the F2N clone, particularly, from the F2N78 cell.

Thus, the human host cell according to an embodiment of the present invention continuously expresses EBNA1 protein, expresses enzymes involved in generating glycosylation profiles similar to those of human, and does not express an IgM protein.

The human host cell according to an embodiment to the present invention provides stable expression of EBNA1. EBNA1 is a gene having a size of about 3 kb and is an essential element for autonomous replication of oriP expression vector in cells. If EBNA1 exists in cis or in trans with the oriP expression vector in cells, the oriP expression vector may be normally replicated in human cells. However, if EBNA1 does not separately exist from the oriP expression vector (in trans), but exists in the oriP expression vector (in cis), the vector DNA may not be easily handled because the expression vector is too large and all genes including the EBNA1 gene may not be efficiently expressed. However, since the EBNA1 protein is continuously expressed from the EBV genome inserted into chromosomes of the F2N78 cell, the oriP plasmid is not required to have the EBNA1 gene. Thus, the oriP expression vector may be efficiently handled, and genes contained in the vector may be easily expressed.

The human host cell according to an embodiment of the present invention also continuously expresses enzymes related to glycosylation profiles similar to those of humans.

Since proteins produced from the human host cell according to an embodiment of the present invention have glycosylation profiles similar to those of humans, the proteins may have lower in vivo immunogenicity and longer in vivo half-life than the proteins produced from non-human cells such as CHO cells, thereby improving efficacy of protein-based pharmaceuticals.

In addition, the human host cell of an embodiment to of the present invention does not express the IgM protein which is expressed in the Namalwa cell. Thus, the human host cell according an embodiment to of the present invention has essential features for producing a therapeutic recombinant monoclonal antibody.

In order to identify anti-apoptotic activity of the F2N78 cell, the F2N78 cell was treated with different concentrations of odium butyrate. In general, sodium butyrate increases the expression of genes by a CMV- or SV40-promoter during the cell cultivation (Lee et al., 1993, Cell 72:73-84, Cockett et al., 1990, Bio/technology 8:662-667, Chang et al., 1999, Free Rad Res 30:85-91, and Gorman et al., 1983, Nucl Acid Res 11:7631-7648). Sodium butyrate also arrests a cell cycle or induces cell differentiation, leading to apoptosis (Cuisset et al., 1998, Biochem Biophy Res Commun 246:760_764, Cuisset et al., 1998, Biochem Biophy Res Commun 246:760_764). However, F2N78 cells according to an embodiment of the present invention shows decrease in apoptosis even in the treatment of sodium butyrate and in some cases, higher growth rate than the control (F2N78 treated with 0 mM sodium butyrate). Namalwa cell, as a control, shows decrease in viability and discontinuation in growth in all conditions after the treatments of sodium butyrate, while 293 cell shows apoptosis when exposed to high concentration of sodium butyrate (See FIGS. 9A to 9D).

In order to identify anti-apoptotic cell growth of the F2N78 cell, the expressions of BHRF1 and BALF1, which are viral bcl-2 homolog genes contained in the EBV genome genes derived from Namalwa cell, were confirmed using RT-PCR. As shown in FIG. 10, BHRF1 was expressed in Namalwa cells both untreated and treated with sodium butyrate. On the other hand, BHRF1 was not expressed in the F2N78 cells either untreated or treated with sodium butyrate. However, BALF1 was expressed in both the Namalwa cell and the F2N78 cell regardless of the treatment with sodium butyrate. Both BHRF1 and BALF1 were not expressed in the 293 cell, as a control. It is reported that BALF1 inhibits anti-apoptotic activity of BHRF1 when both BALF1 and BHRF1 are simultaneously expressed (Bellows et al., 2002, J. Virol. 76:2469-2479, Marshall et al., 1999, J. Virol. 73:5181-5185). This feature is found in the Namalwa cell. Thus, the result described above showing that only BALF1 is expressed in the F2N78 cell may prove the anti-apoptotic activity of the F2N78 cell. This feature is also found in other clones than F2N78. Since this result is not expected, reasons and mechanisms therefor are yet to be identified.

Thus, the human host cell according to an embodiment to of the present invention shows anti-apoptotic activity when cultured in the presence of sodium butyrate. This invention indicates that the human host cell according to an embodiment to of the present invention may also have resistance to naturally-occurring apoptosis during a long-term batch culture even when sodium butyrate is not added to the culture medium.

Two cell lines producing antibodies, i.e., a CHO cell and an F2N78 cell, are compared with each other in order to identify antibody productivity of the F2N78 cell when treated with sodium butyrate. The cell growth rate of the CHO cell line treated with sodium butyrate is reduced by 50%, and the productivity of the CHO cell is doubled when compared with a control which is not treated with sodium butyrate (See FIG. 11). On the other hand, the cell growth rate of the F2N78 cell treated with sodium butyrate is increased by up to 2 times, and the productivity of the F2N78 cell is increased by 4 to 5 times when compared with a control which is not treated with sodium butyrate (See FIG. 12). This may indicate that the anti-apoptosis of the F2N78 cell treated with sodium butyrate influences the increase in productivity of antibodies.

In order to identify antibody productivity of the oriP expression vector in the F2N78 cell, the F2N78 cell was transfected with a pCT132 expression vector or a pCT125 expression vector, and then antibody productivities were compared. While the pCT125 expression vector includes an EBNA1 coding sequence in the plasmid, the pCT132 expression vector does not include the EBNA1 coding sequence in the plasmid. As shown in FIG. 7, cells transfected with the pCT132 expression vector exhibits comparable or higher antibody productivity when compared with cells transfected with the pCT125 expression vector. In general, it is advantageous to use a transient transfection to produce, in a short period of time, a small amount of protein required in the process of new drug development. Thus, since the human host cell according to an embodiment to of the present invention continuously expresses EBNA1, the cell may be suitably used for the new drug development based on the transient transfection using an EBNA1 gene free expression vector such as the pCT132 expression vector.

The human host cell according to an embodiment to of the present invention may be used to produce recombinant proteins. The human host cell may be genetically engineered in order to express a variety of recombinant proteins. The recombinant proteins may include human therapeutic recombinant proteins, for example, therapeutic monoclonal antibodies, and therapeutic recombinant proteins other than the monoclonal antibodies.

Advantageous Effects

The present invention provides a human host cell generated from fusion of a human embryonic kidney-derived cell and a human B-cell-derived cell with an Epstein-Barr virus (EBV) genome inserted into its chromosomes. Using the human host cell of an embodiment to of the present invention, proteins for research may be produced in a short period of time, and heterologous recombinant protein-based pharmaceuticals for human use may be produced with high quantity and quality.

BRIEF DESCRIPTION OF THE DRAWINGS

The above and other features and advantages of the present invention will become more apparent by describing in detail exemplary embodiments thereof with reference to the attached drawings.

FIGS. 4A to 4C illustrate results of transient transfection performed to select F2N clones with high IgG expression, wherein FIG. 4A illustrates results of a first screening, FIG. 4B illustrates results of a second screening of firstly selected 17 clones, and FIG. 4C illustrates results of comparison of IgG productivity between the finally selected F2N78 cells and 293 cells. The results shown here are obtained from triplicate experiments.

MODE OF THE INVENTION

Hereinafter, the present invention will be described in greater detail with reference to the following examples. The following examples are for illustrative purposes only and are not intended to limit the scope of the invention.

Materials and Methods

1. Cell and Plasmid

Human embryonic kidney (293) cell (ATCC CRL-1573) and Namalwa cell (ATCC CRL-1432) were obtained from the American Type Culture Collection (ATCC).

Figure 3:
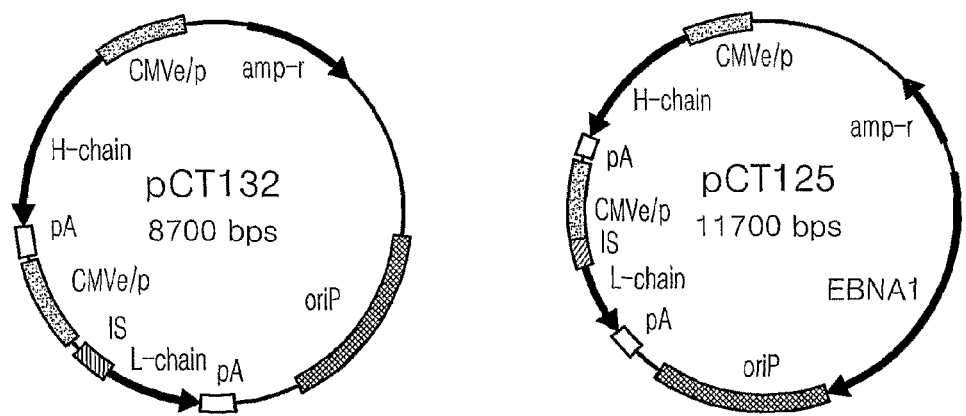
FIG. 3 illustrates cleavage maps of expression vectors used herein, all of which are built based on a pCT vector.

FIG. 3 illustrates cleavage maps of expression vectors used herein.

2. Transfection

Electrophoration and a cationic polymer-based method were used for transfection.

Electrophoration: $3\times10^6$ cells were resuspended in 300 μl of a RPMI 1640 medium containing 12 μg of a plasmid (pSV2neo vector (2 μg) and a vector with a matrix attached region (MAR) sequence (10 μg)). Electrophoration was performed using a GenePulse II electrophorator (Bio-Rad) (220V/960 microfarads). Then, the resultant was suspended in a growth medium and 72 hours later, was cultured in a selective medium supplemented with 1 mg/ml G418 and 10% fetal bovine serum (FBS) for about 14 days. It was found that transfected cells actively grew, while control cells did not grow in the selective media. The transfected cells were selected and further cultured in a selective medium supplemented with 1 mg/ml G418. The existence of a neomycin gene was identified by performing a polymerase chain reaction (PCR) using the neomycin gene specific primer.

Cationic polymer-based method: Lipofectamine™ LTX (Invitrogen, 15338-100) and FreeStyle™ Max (Invitrogen, 16447-100) were used as cationic polymers, and transfections were performed according to the manufacturer's instructions. When using the Lipofectamine™ LTX reagent, a 6-well plate was seeded with cells one day prior to transfection such that the saturation of the cells reached 50 to 80% per well on the day of transfection. 2.5 μg of DNA and 6.25 μl of LTX were used to perform the transfection. When using the FreeStyle™ Max reagent, transfection was performed in suspension culture. Cells, which grow in a serum free medium, i.e., a FreeStyle 293 Expression medium (Invitrogen, 12338, hereinafter referred to as FreeStyle 293 medium) or an EX-CELL 293 Serum free medium (Sigma, 14571C, hereinafter referred to as EX-CELL 293 medium), were seeded such that the concentration of the cells were adjusted to $1\times10^6$ cells per 1 ml on the day of the transfection. The transfection was performed in an OptiPRO SFM II (Invitrogen, 12309) medium with addition of DNA and FreeStyle™ Max reagent in a ratio of 1:1.

3. Immunofluorescence (IF)

In order to detect the expression of EBNA1, cells were reacted with a fluorescent dye-conjugated anti-serum protein (ACIF) (Reedman and Klein, 1973 and Fresen and zur Hausen, 1976). First, cells were smeared on a slide glass and fixed using methanol at −20□ for 5 minutes. As a first reaction antibody, human serum having a high anti-EBNA titer was used to react with the cells. Then, the cells were treated with human complement (serum protein) to amplify signals form EBNA1, and the EBNA1 dyeing was detected using a fluorescent material-conjugated anti-human complement C3 antibody (FITC-conjugated anti human complement C3 antibody, USBiological, C7850-14C). The resulting slide was treated with a solution of glycerol and a phosphate buffer in a ratio of 1:1.

In order to detect the expressions of Ig-mu and Ig-kappa, cells were treated with a fluorescent material-conjugated anti-human IgM antibody (FITC-conjugated affinity-purified goat anti-human IgM, mu chain specific, Sigma, F5384) and a fluorescent material-conjugated anti-human kappa chain (Fluorescein anti-human kappa chain, affinity purified made in goat, Vector, FI-3060) in the same manner as described above.

In order to detect the expression of α(2,6)ST protein, cells were treated with a fluorescent material-conjugated *Sambucus nigra* lectin (FITC conjugated Sambuicus nigra (Elderberry bark)-SNA-1, EY laboratories, F-2602) in the same manner as described above.

4. RT-PCR of EBNA1, GnTIII, Ig-mu, BALF1, BHRF1 mRNA was extracted from cells using a RNeasy®Plus Mini kit (Qiagen, 74134), and RT-PCR was performed using a OneStep RT-PCR Kit (Qiagen, 210212). Each of the primer sequences are shown in Table 1 below. The RT-PCR was performed using a GeneAmp PCR system 9700 (Applied Biosystems), and stages and conditions for the RT-PCR were as follows: (i) reverse transcription (1 cycle of 50° C. for 30 minutes); (ii) inactivation of reverse transcriptase and cDNA denaturation (1 cycle of 95□ for 15 minutes); (iii) PCR amplification (35 cycles of 94° C. for 30 seconds, 52° C. for 1 minute, and 72° C. for 30 seconds); and (iv) elongation (1 cycle of 72° C. for 10 minutes). Products of the RT-PCR were identified using agarose gel electrophoresis.

TABLE 1

Primer sequences used in RT-PCR

| Primer | Primer sequence (5' to 3') Direction | Length (bp) | Genebank No. |
|---|---|---|---|
| GnTIII-1 | GACGTGGTGGACGCCTTTGT sense (SEQ ID NO: 1)<br>CGACCACTGCACCAGATGT antisense (SEQ ID NO: 2) | 533 | NM002409 |
| GnTIII-2 | CAAGGTGCTCTATGTCTTCCTGGAC sense (SEQ ID NO: 3)<br>CGGTCGTAGTTCTTAGCAGGTAC antisense (SEQ ID NO: 4) | 678 | |
| Ig-mu | ACAAGGTGACCAGCACACTGAC sense (SEQ ID NO: 5)<br>GTGACGGTGGTACTGTAGAAGAGGC antisense (SEQ ID NO: 6) | 879 | BC020240 |
| EBNA1-1 | GTCCAAGTTGCATTGGCTGC sense (SEQ ID NO: 7)<br>CTCATCTCCATCACCTCCTTCA antisense (SEQ ID NO: 8) | 788 | AY825078 |
| EBNA1-2 | AGAAGGTGCCCAGATGGTG sense (SEQ ID NO: 9)<br>CTCATCTCCATCACCTCCTTCA antisense (SEQ ID NO: 10) | 759 | P207MnA5 |
| BHRF1 | TACGCATTAGAGACCTACTTGAGCC sense (SEQ ID NO: 11)<br>GTCAAGGTTTCGTCTGTGTG antisense (SEQ ID NO: 12) | 1000 | V01555 |
| BALF1 | GAGGCCAGCCAAGTCTACAGATTC sense (SEQ ID NO: 13)<br>GAACTGACGTCTCAGCGATCTTG antisense (SEQ ID NO: 14) | 550 | |

5. Enzyme-Linked Immunosorbent Assay (ELISA)

The concentration of secreted antibodies was measured using an enzyme-linked immunosorbent assay (ELISA). First, goat anti-human immunoglobulin G(Fcγ) (Jackson ImmunoReserarch, 109-006-098) was adsorbed onto a 96-well microtiter plate (Nunc, 449824). The plate was blocked by treatment with a 1% bovine serum albumin (BSA) containing phosphate buffer, and 2-fold serial dilutions of the sample were placed in each of the wells on the plate. The plate was incubated at room temperature for 2 hours, and was treated with a peroxidase-labeled goat anti-human λ antibody (Sigma, A5175) for detection. The resultant was incubated at room temperature for 1 hour and reacted with tetramethyl benzidine (TMB), and the reaction was terminated using 1 N HCl. The human IgG1 lambda purified from myeloma plasma (Sigma, 15029) was used as a standard from a concentration of 250 ng/ml. The concentration of antibodies was measured based on absorbance at 450/570 nm using a Spectramax plus 384, Molecular Device.

EXAMPLE 1

Generation of Human Cell Line by Cell Fusion

First, a Namalwa cell line was cultured in RPMI1640 medium supplemented with 10% FBS (Hyclone, SH30070.03) and 6-thioguanine (Sigma, A4660) in order to obtain a HAT(Sigma, H0262)-sensitive and G418(Calbiochem, 345810)-resistant Namalwa cell as a cell fusion partner. During a selection period of 4 months, the Namalwa cell line was treated with growing concentrations of 6-thioguanine from 5 µg/ml to 30 µg/ml, and sensitivity of the Namalwa cell to a 1×HAT-containing medium was identified. The HAT-sensitive Namalwa cell population was transfected with pSV2neo plasmid, and then cells having resistance to 1.5 mg/ml G418 were selected to be used as the cell fusion partner.

Figure 1:
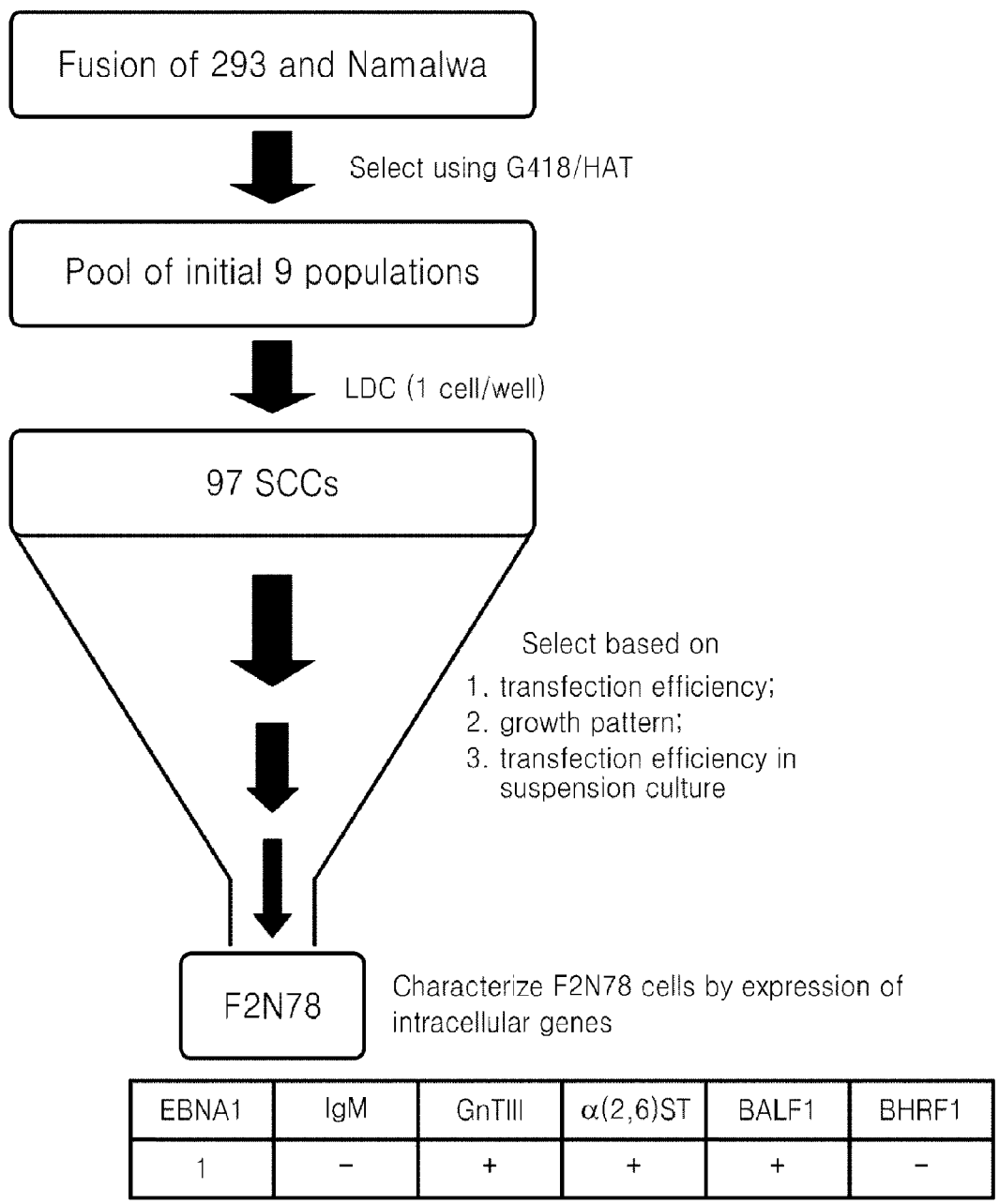
FIG. 1 illustrates a process of fusion of an F2N cell and selection of F2N78 clones.
Figure 2:
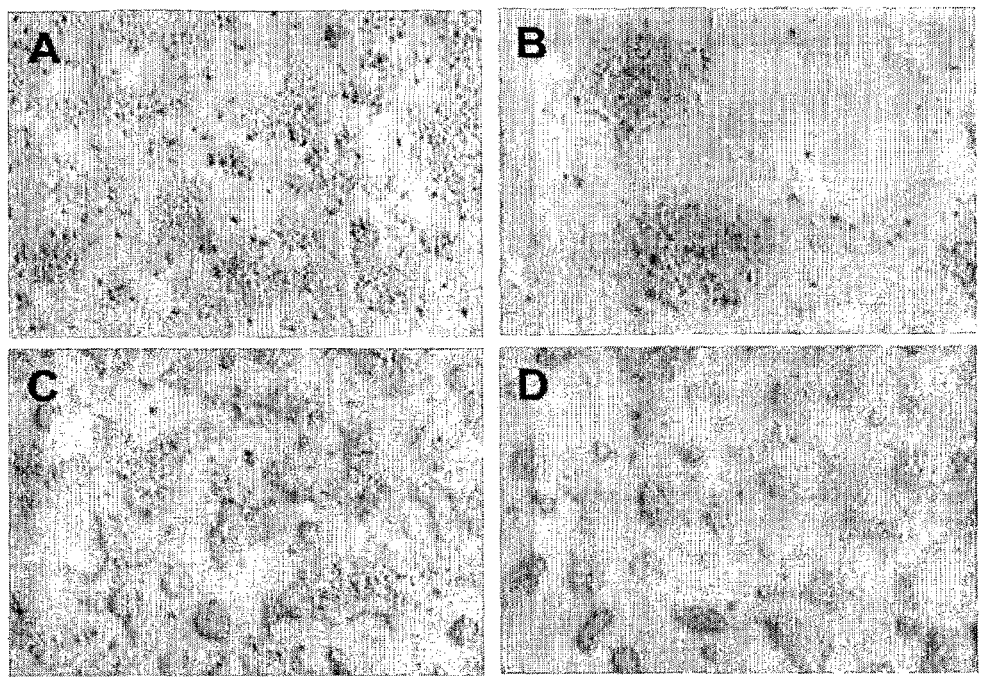
FIGS. 2A to 2D illustrate various growth patterns of an F2N clone at an initial stage, wherein clones grown in aggregates as shown in FIGS. 2C and 2D are removed in a selection process.

The cell fusion was performed using polyethyolene glycol (PEG) according to a method disclosed in Kennett RH. Cell fusion. Methods Enzymol 58:345-359; 1979. $4 \times 10^6$ 293 cells and $6 \times 10^6$ Namalwa cells in the logarithmic growth phase, were washed twice with a calcium ($Ca^{2+}$) and magnesium ($Mg^{2+}$)-free phosphate buffer, and seeded onto a 6-well plate pre-treated with 5 µg/ml peanut agglutinin (Sigma, L0881). The 6-well plate was centrifuged at 400 g for 6 minutes (in Beckman Allegra™ X-12R centrifuge). The phosphate buffer was removed from the wells, and the cells in the wells were treated with 2 ml of 40% polyethylene glycol (Sigma, P7777) for 2 minutes. Cells in one of the wells were not treated with polyethylene glycol as a control. Then, the cells were washed three times with 5 ml of a phosphate buffer including 5% dimethyl sulphoxide (DMSO; Sigma, D2650), and washed three times with a phosphate buffer. The cells were treated with a culture medium of a DMEM/F12 medium and a RPMI1640 medium mixed at a ratio of 1:1 supplemented with 15% FBS. The cells were maintained in a $CO_2$ incubator for 30 minutes. Then, the culture medium was removed, and the cells were treated with a selective medium supplemented with 0.4 mg/ml G418, 0.5×HAT, and 15% FBS, wherein a DMEM/F12 and a RPMI1640 were mixed in equal amounts. $1 \times 10^4$ cells were seeded onto each well of the 96-well plate. After one week, the culture medium was exchanged with a fresh selective medium having the same composition as that used when the cells were seeded. After two weeks from the seeding, a selective medium having 0.8 mg/ml G418 and 1×HAT was supplied to the cells. After three weeks from the seeding, it was observed that control cells did not grow, but the fused cells grew. Cells, which grew rapidly and well, were combined from 9 wells, and the cells were subjected to limiting dilution cloning (LDC) in a 96-well plate to prepare a single cell clone (SCC). During the limiting dilution cloning, a single cell among logarithmically growing cells was seeded onto each well of a 96-well plate with 100 µl of a selective medium, and a fresh medium supplemented with 0.8 mg/ml G418, 1×HAT, and 15% FBS was used as the selective medium. A fresh selective medium was supplied to the cells every week, and each of the wells was observed under a microscope in order to identify whether the single cell seeded onto each well grew. Through the above process, 97 single cell clones were obtained, and designated F2N. The F2N is a cell generated from the fusion of the 293 cell and the Namalwa cell. The growth pattern of each of the F2N clones is similar to that of the 293 cell since the F2N clone was suspension-cultured while somewhat adsorbed onto the bottom of the slide glass, and formed a tightly aggregated patch. All clones were preserved frozen in a nitrogen tank. The expressions of EBNA1 and IgM, and transfection efficiency were measured from all the clones. As a result, it was found that all of the clones expressed EBNA1. The expression of EBNA1 indicates the existence of EBV in the clones. In addition, it was found that all of the clones did not express IgM, which indicates that the expression of immunoglobulin of the Namalwa cell was inhibited in the fused cells. For more systematic characterization, 17 clones, exhibiting a favorable growth pattern and high transfection efficiency, were selected. The transfection efficiency of the selected 17 F2N clones was higher than that of the 293 cell when tested with the pCT132 vector expressing IgG. In the process of selecting the 17 F2N clones, single cell clones, which grew in aggregates, were excluded (See FIGS. 2C and 2D).

EXAMPLE 2

Examination of Features of F2N78 Clones

Figure 4A:
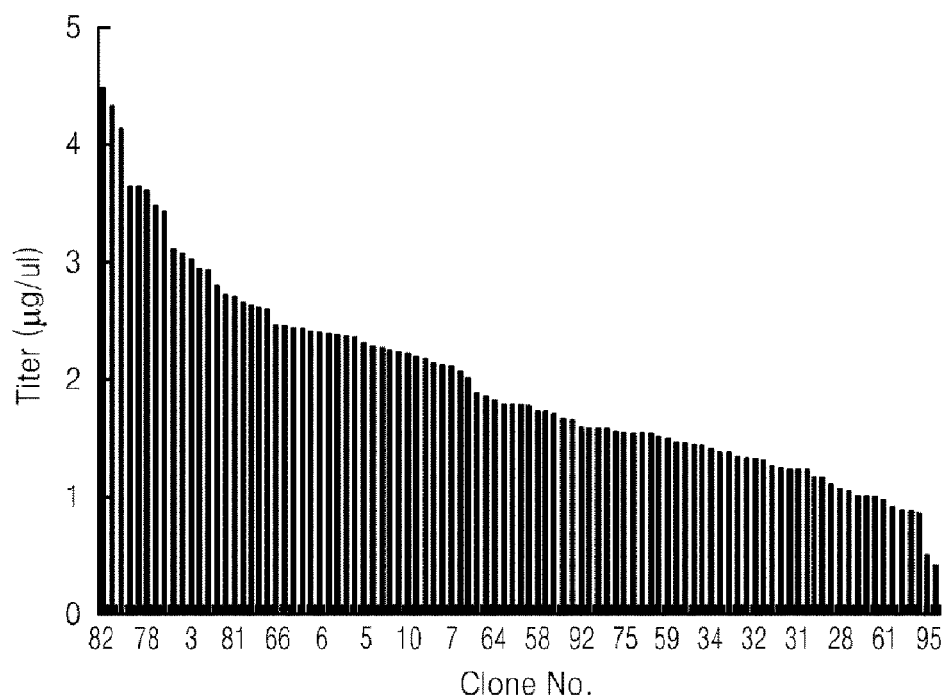
Figure 4B:
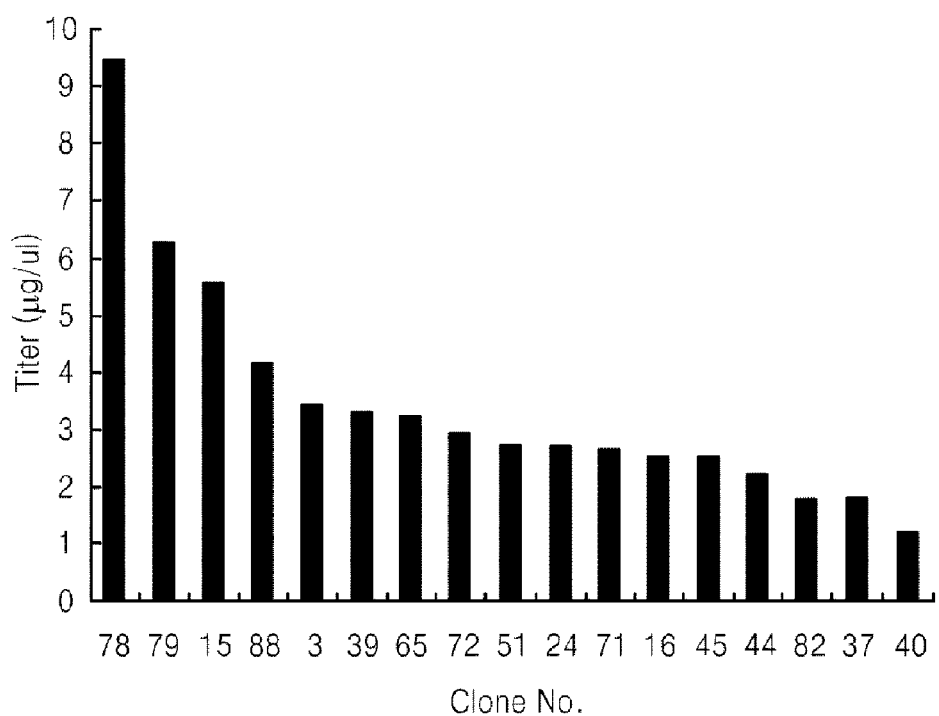
Figure 4C:
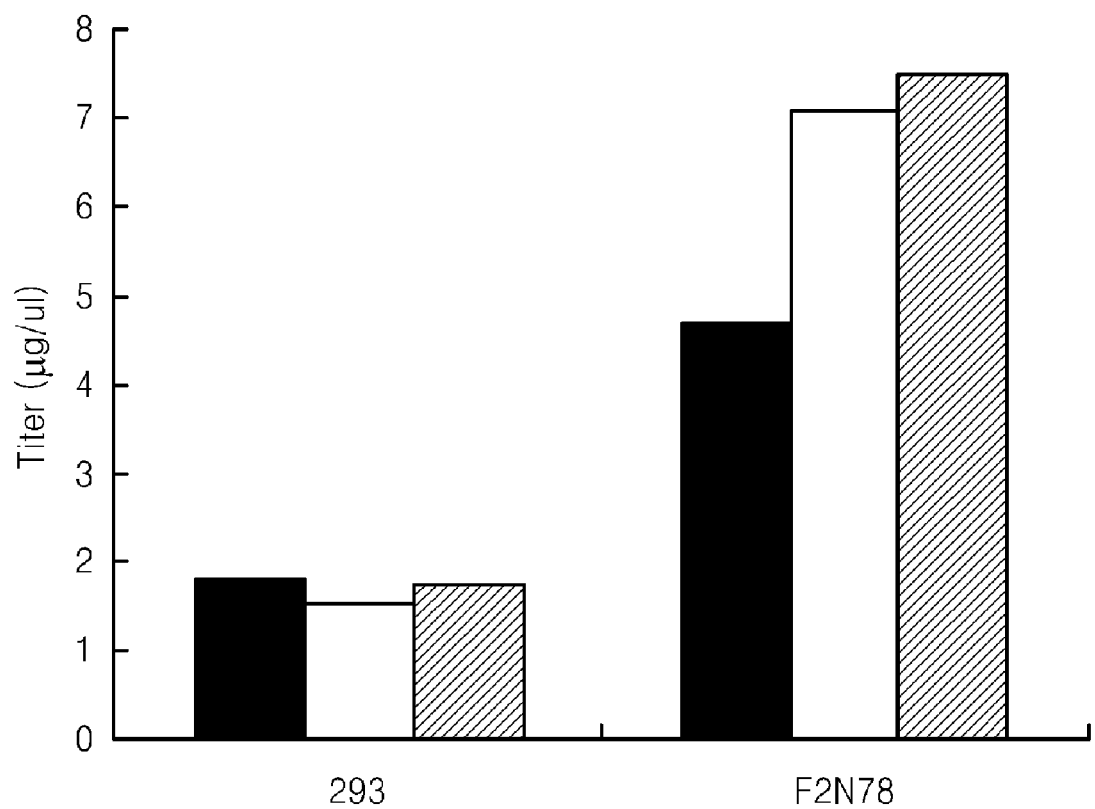

Firstly, 17 clones having high IgG expression were selected using a transient transfection for the selection of F2N clones (See FIG. 4A). Then, these clones were subject to a second screening (See FIG. 4B). In order to compare IgG productivities between the F2N78 cell having the highest IgG expression and the 293 cell, the transient transfection was repeatedly performed using the pCT132 vector. As a result, it was found that the IgG expression rate of the F2N78 cell was 2 to 3 times higher than that of the 293 cell (See FIG. 4C).

Figure 5A:
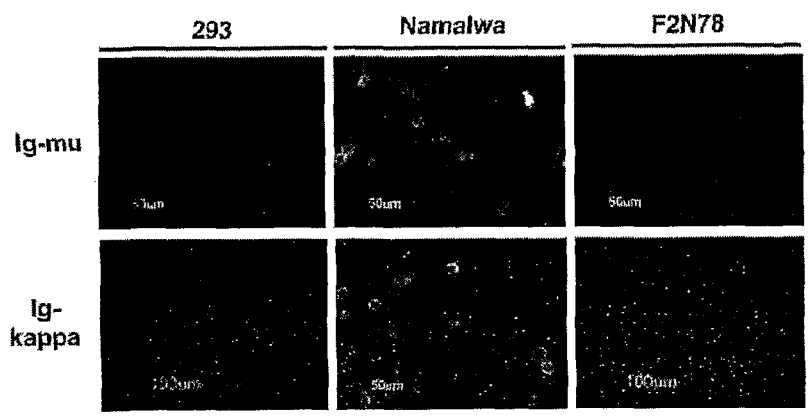
FIG. 5A illustrates expressions of Ig-mu and Ig-kappa.
Figure 5B:
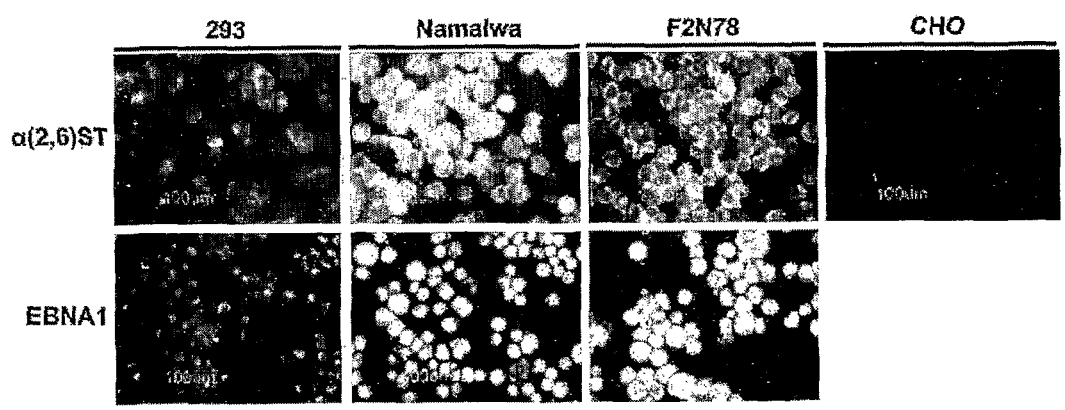
FIG. 5B illustrates expressions of EBNA1 and α(2,6)—ST using Immunofluorescence.

All of the firstly selected 17 clones were positive for EBNA1 expression and negative for IgM expression. 7 single cell clones among the 17 single cell clones were selected based on IgG expression efficiency and adapted to grow in serum free suspension culture. The continuous expression of EBNA1 was used to identify whether the 7 single cell clones, which were adapted to grow in serum free suspension culture, include an EBV genome. As shown in FIG. 5, almost 100% of the F2N78 cell population which had grown for 1 year or more under serum free culture conditions was positive for EBNA1 expression. One year may be sufficient for division of the cell clones in the production of therapeutic proteins including time required to develop and produce a master cell bank (MCB) and a master working cell bank (MWCB).

Figure 6:
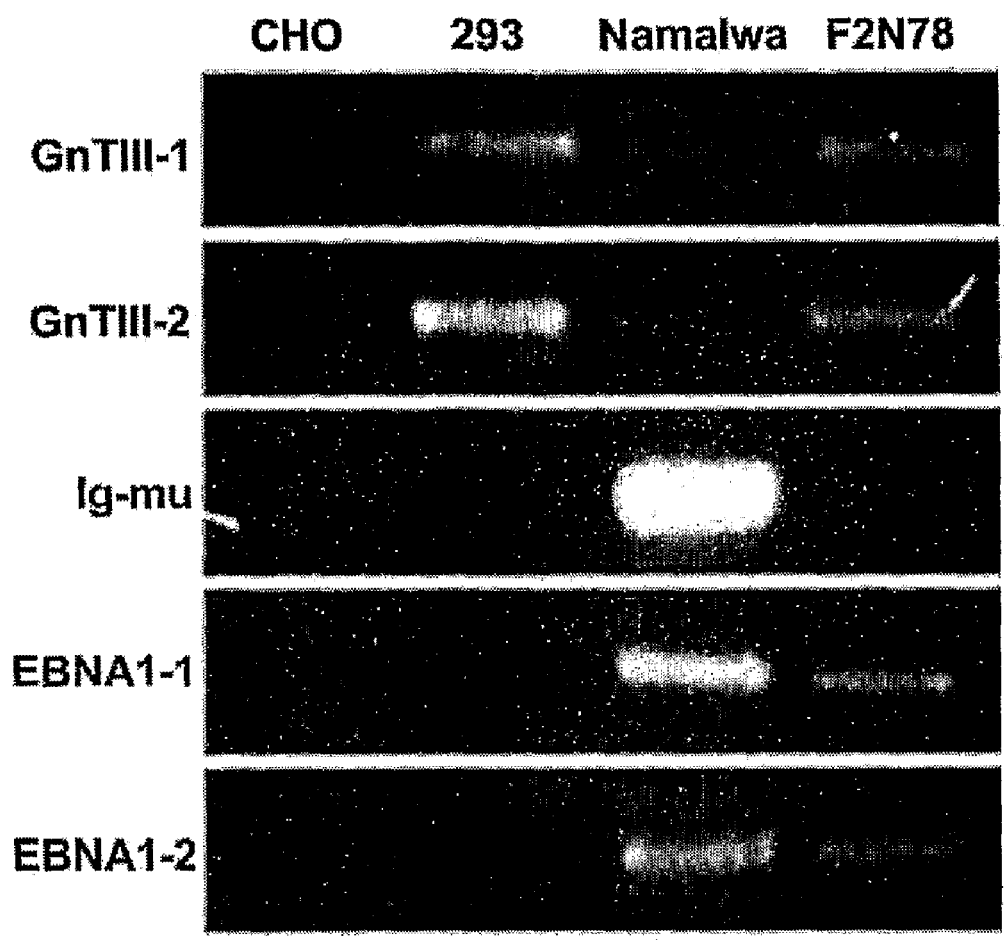
FIG. 6 illustrates expressions of GntIII, Ig-mu, and EBNA1 in F2N78 cells using reverse transcription-polymerase chain reaction (RT-PCR), wherein a Namalwa cell, a 293 cell, and a CHO cell are used as negative controls. Primer specific to GntIII, Ig-mu, and EBNA1 proteins are shown in Table 1.

IF (FIG. 5) and RT-PCR (See FIG. 6) of the F2N78 clones, which had been cultured for 1 year or more in serum free suspension culture, were performed in order to detect continuous expression of important genes in cells. The results are as follows: (1) the expression of EBNA1 was identified using IF and RT-PCR using two different types of primer pairs; (2) extinction of Ig-mu expression was identified using IF and RT-PCR, and extinction of Ig-kappa expression was identified using IF; (3) the expression of GnTIII (Campbell and Stanley, 1984) involved in the production of bisecting N-acetylglucosamine which is closely related to antibody dependant cellular cytotoxicity was identified by RT-PCT using two different types of primer pairs; and (4) the expression of α(2,6)ST, which exists not in CHO cells but in human cells, was identified by IF.

EXAMPLE 3

Transient Transfection

A transient transfection has been used to produce, in a short period of time, protein required to develop a new drug. For this, a F2N78 cell and a 293 cell suspension-cultured in FreeStyle 293 medium were transfected with two oriP expression vectors having different structures, pCT132 and pCT125, and antibody productivities were compared with each other. The pCT125 vector includes an EBNA1 coding sequence in plasmid, while the pCT132 expression vector does not include the EBNA1 coding sequence in plasmid.

Figure 7:
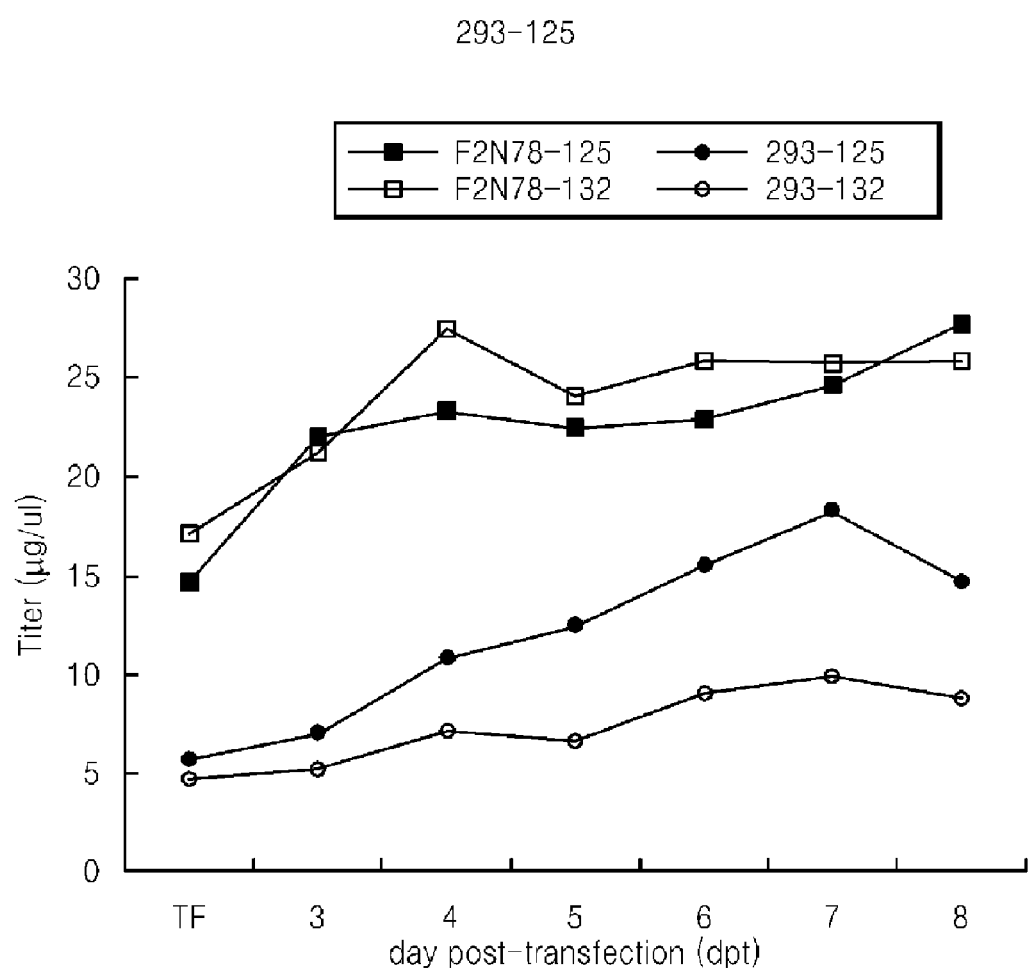
FIG. 7 is a graph illustrating antibody productivity of an oriP expression vector (pCT125 and pCT132) in an F2N78 cell and a 293 cell.

As shown in FIG. 7, in repeatedly performed transfections of the F2N78 cell and the 293 cell with the pCT132 and the pCT125, both of the vectors exhibited similar antibody productivity to each other in the F2N78 cell, but the IgG productivity of the pCT 125 was higher than that of the pCT132 in the 293 cell. Furthermore, the amount of IgG produced by the F2N78 cell transfected with the pCT132 vector (equal to or greater than 25 µg/ml) was greater than that produced by the 293 cell transfected with the pCT125 vector (15 µg/ml). Thus, the production efficiency of IgG produced by the pCT132 expression vector without an EBNA1 gene in the F2N78 cell was higher than that of IgG produced by the pCT125 expression vector with EBNA1 gene in the 293 cell. On the other hand, in the 293 cell in which EBNA1 was not expressed, the pCT125 expression vector with EBNA1 has greater IgG production efficiency than the pCT132 expression vector without EBNA1.

Figure 8:
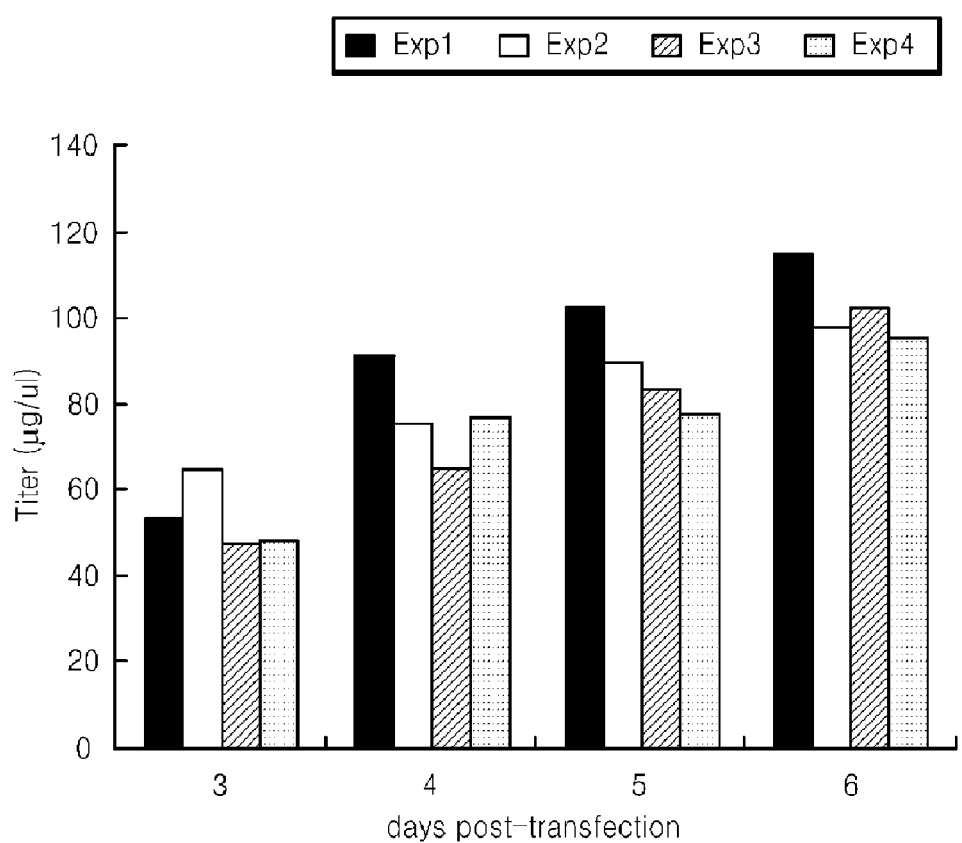
FIG. 8 is a graph illustrating antibody productivity by performing a transient transfection of an F2N78 cell with pCT132, which is an expression vector without an EBNA1 gene. The results shown here are obtained from 4 repetitive experiments.
Figure 9A:
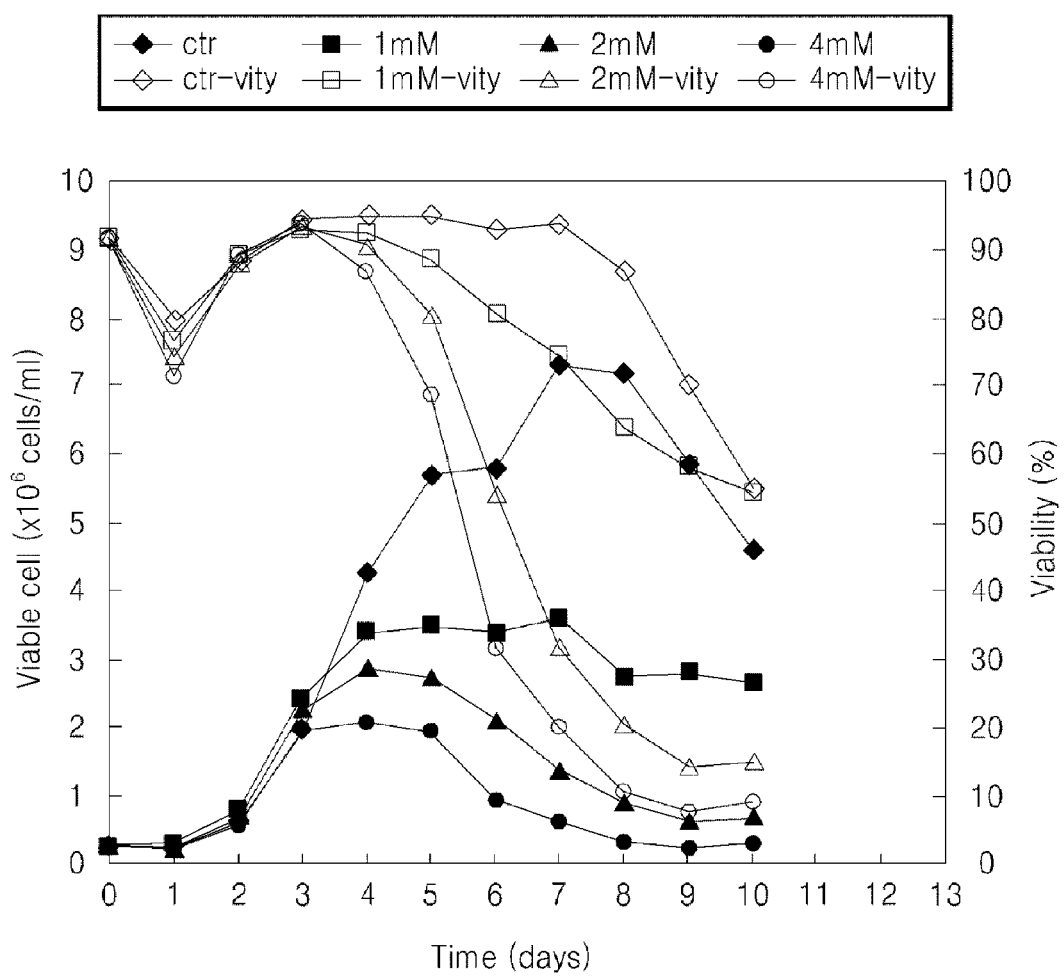
FIGS. 9A to 9D are graphs respectively illustrating effects of sodium butyrate on cell growth of a CHO cell (FIG. 9A), a Namalwa cell (FIG. 9B), a 293 cell (FIG. 9C), and an F2N78 cell (FIG. 9D).
Figure 9B:
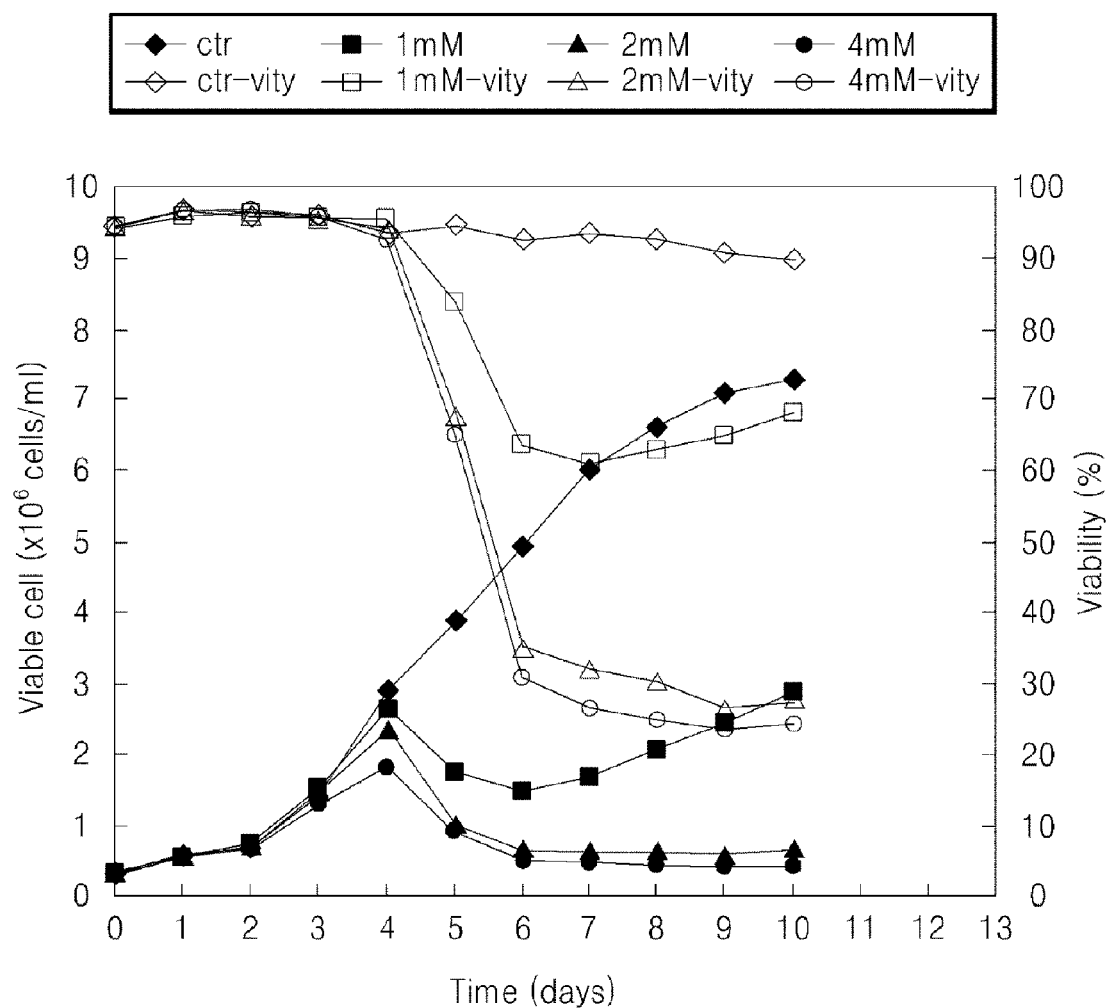
Figure 9C:
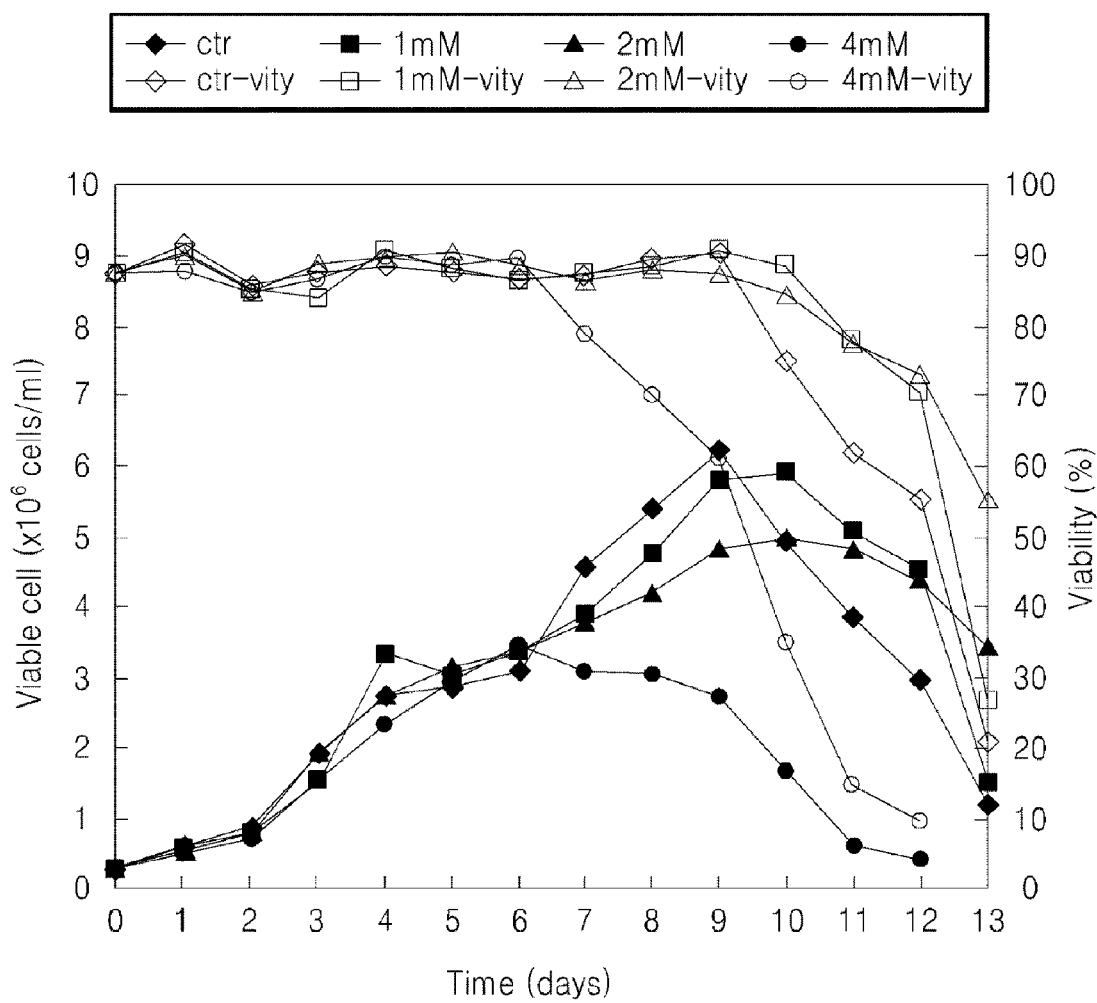
Figure 9D:
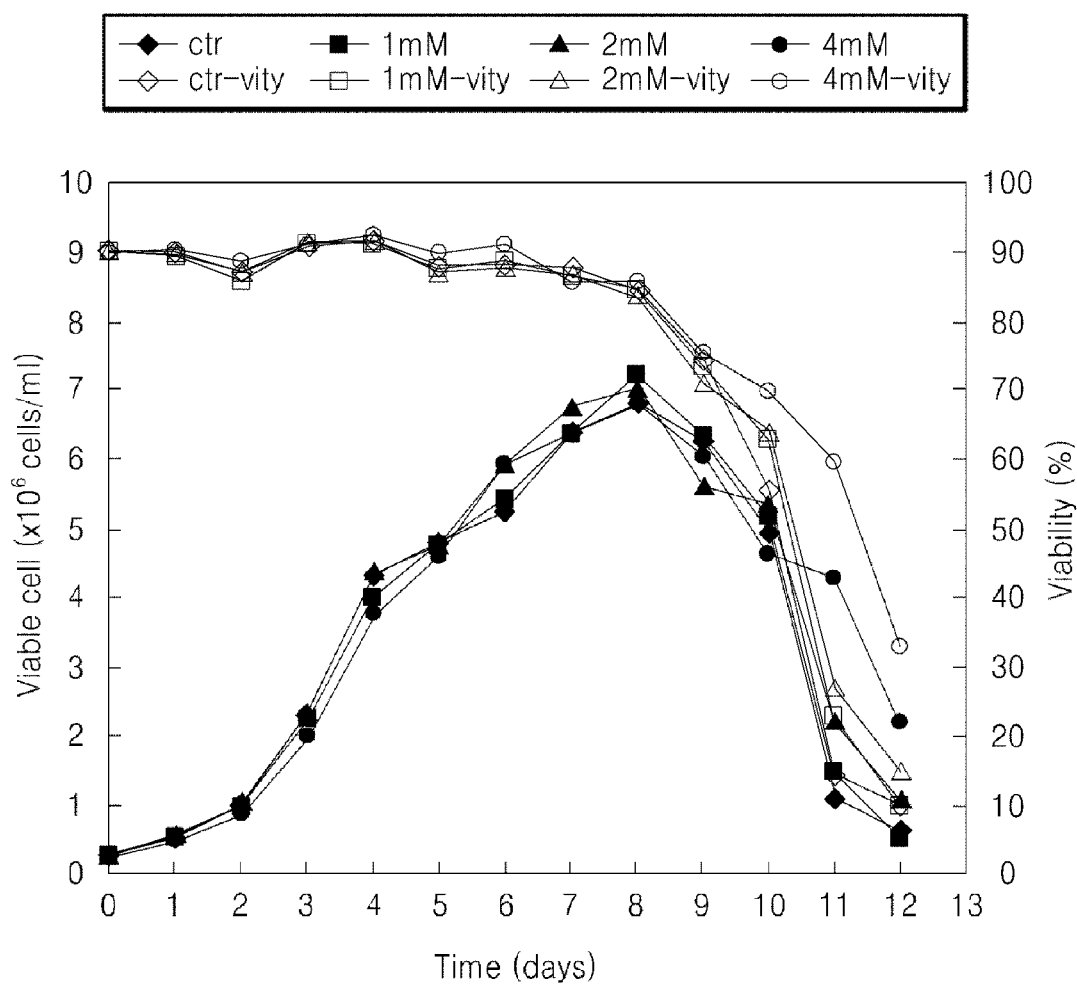

In order to increase efficiency of the pCT132 expression vector, the F2N78 cell was adapted to growth in a EX-CELL 293 medium, and a transient transfection was performed using a FreeStyle Max reagent. As a result, excellent antibody productivity of about 100 µg/ml was identified 6 days after the transient transfection in replicate tests (See FIG. 8). This result indicates that transfection efficiency of the human host cell according to the present invention is higher than that of the 293 cell line.

EXAMPLE 4

Effects of the Treatment of Sodium Butyrate to F2N Cell

The treatment of sodium butyrate influences production cell lines in two ways. The treatment of sodium butyrate activates expression of genes by hyper-acetylation but reduces cell growth rates by inducing apoptosis. CHO cells, 293 cells, Namalwa cells, and F2N78 cells, which were adapted to grow in EX-CELL 293, were seeded such that the concentration of the cells was adjusted to $3 \times 10^5$ per 1 ml, and were treated with different concentrations of sodium butyrate (0, 1, 2, and 4 mM) on the third day.

As shown in FIGS. 9A to 9D, the cell number and cell viability of the CHO cells rapidly decreased as the concentration of sodium butyrate increased. The cell number and cell viability of the Namalwa cells also rapidly decreased in all concentrations of sodium butyrate treated in the similar manner as in the CHO cells. On the other hand, the growth rate of the 293 cells was not influenced by low concentration of sodium butyrate (1 mM and 2 mM), but the growth rate and viability of the 293 cell significantly decreased at a high concentration of sodium butyrate (4 mM). However, the growth rate and viability of the F2N78 cells did not decrease under all conditions, but increased at a high concentration of sodium butyrate (4 mM).

Figure 10:
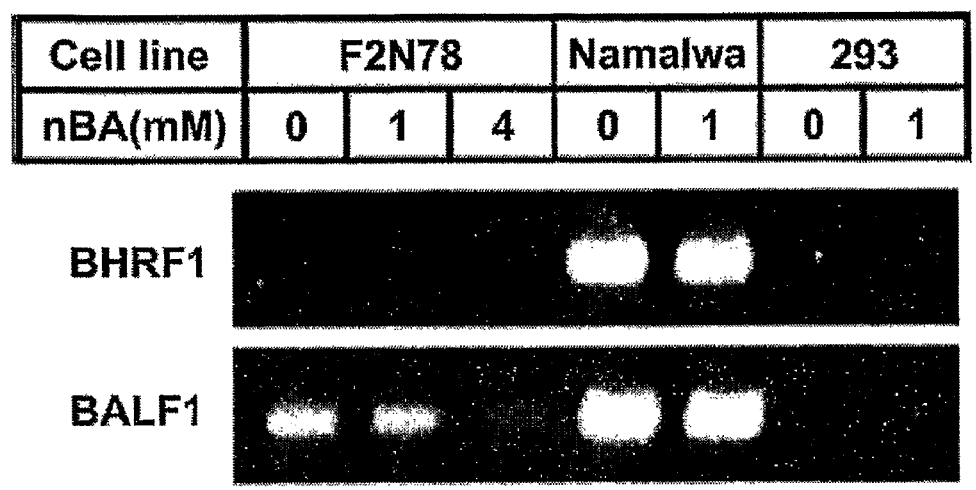
FIG. 10 illustrates expression of BHRF1 and BALF1 in the F2N78 cell, a Namalwa cell, and 293 cell treated with sodium butyrate, using RT-PCR, wherein 0, 1, and 4 indicate the concentrations (mM) of sodium butyrate respectively added to each of culture media.

In order to identify anti-apoptotic cell growth of the F2N78 cell, the expressions of BHRF1 and BALF1, which are viral bcl-2 homolog genes contained in the EBV genome genes derived from Namalwa cell, were identified using RT-PCR. As shown in FIG. 10, BHRF1 was not expressed and BALF1 was expressed in the F2N78 cells both untreated and treated with sodium butyrate. On the other hand, both BHRF1 and BALF1 were expressed in Namalwa cells. Both of BHRF1 and BALF1 were not expressed in the 293 cell, used as a control. The anti-apoptotic cell growth of the F2N78 cell is supported by the fact that BHRF1 is not expressed in the F2N78 cell, even though the F2N78 cell is derived from the Namalwa cell. It has been reported that BALF1 inhibits anti-apoptotic activity of BHRF1 when both BALF1 and BHRF1 are simultaneously expressed (Marshall et al., 1999, J. Virol. 73:5181-5185). Thus, the fact that only BALF1 is expressed in the F2N78 cell may prove the anti-apoptotic activity of the F2N78 cell. However, since both factors are expressed in the Namalwa cell, it is believed that anti-apoptotic cell growth is not observed in the Namalwa cell, unlike in F2N78 cells.

Figure 11:
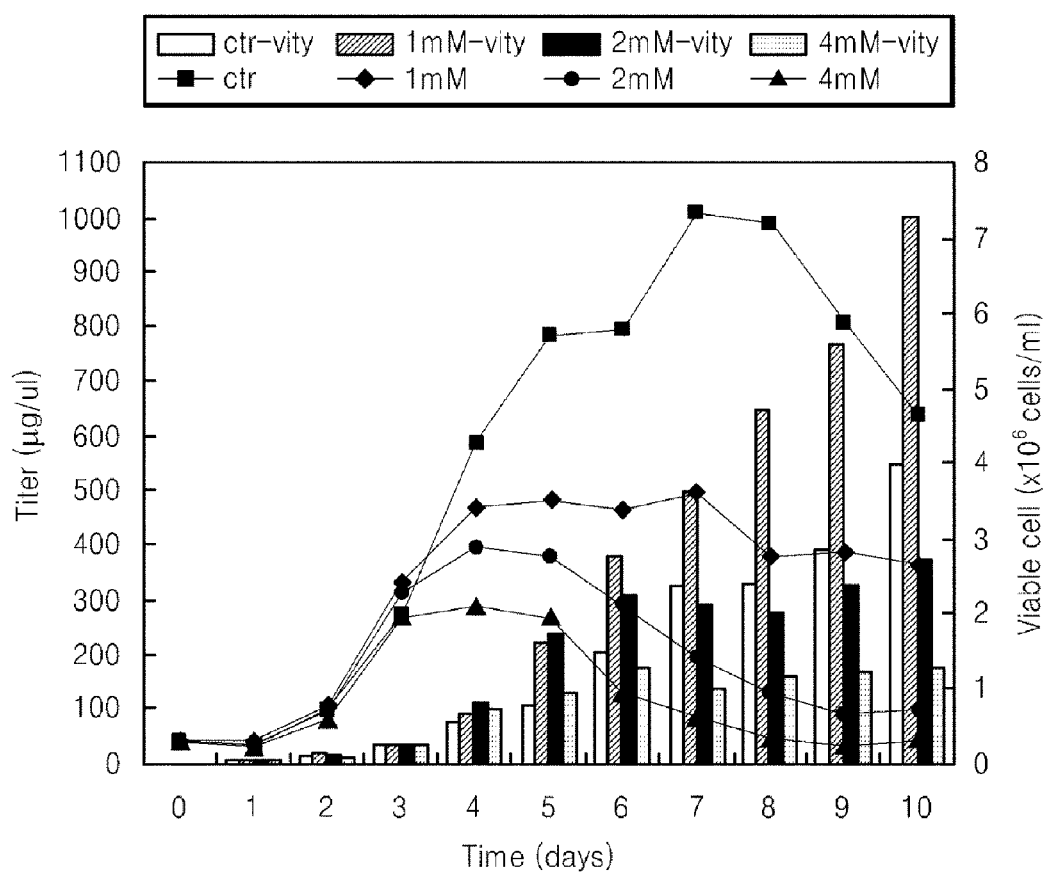
FIG. 11 is a graph illustrating effects of sodium butyrate on antibody productivity of CHO#247 cell.
Figure 12:
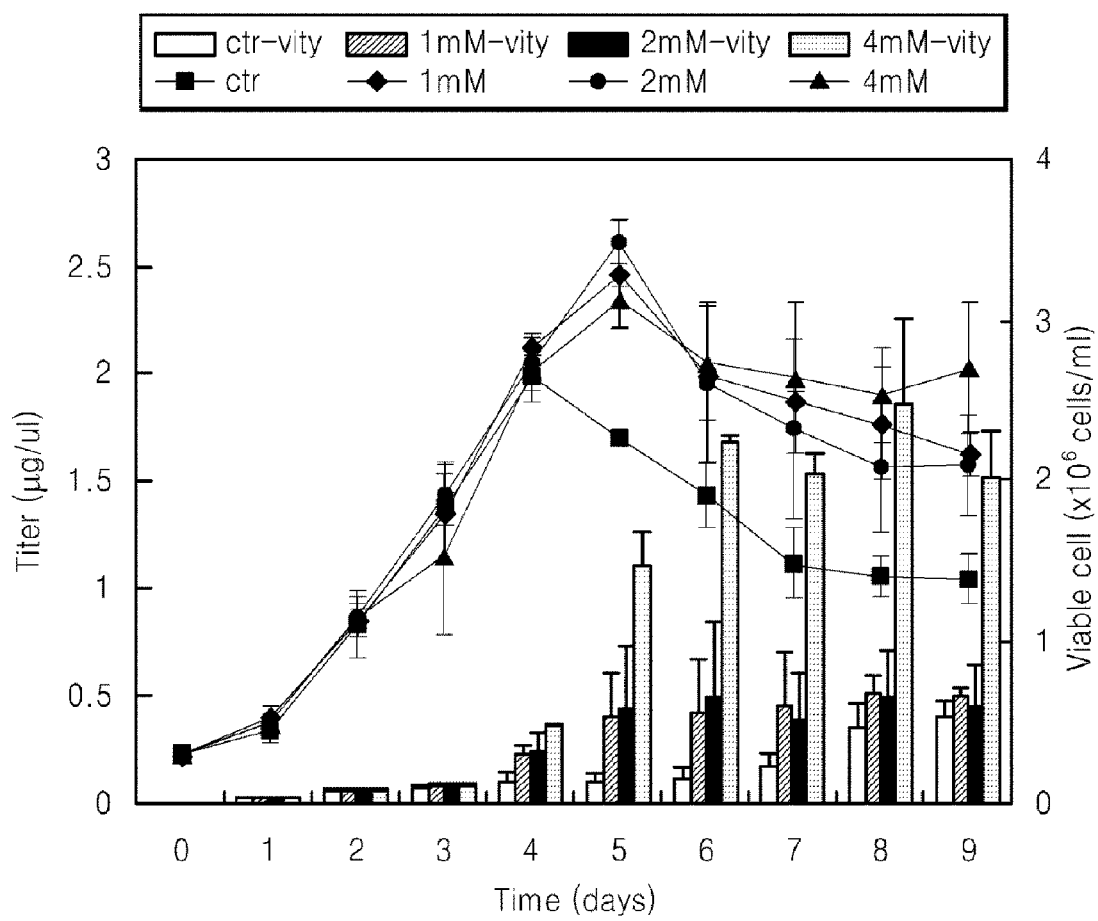
FIG. 12 is a graph illustrating effects of sodium butyrate on antibody productivity of an F2N78_Ig cell.

Then, cell lines producing antibodies were prepared from the CHO cell and the F2N78 cell to identify influence of sodium butyrate on the antibody productivity. CHO#247 is a single cell line for antibody production, prepared by MTX amplification, and F2N78_Ig is a cell line for antibody production, prepared by puromycin selection. Each of the cell lines was seeded and the cell lines were treated with different concentrations (0, 1, 2, and 4 mM) of sodium butyrate on the third day. The cell growth rate of the CHO#247 treated with sodium butyrate was reduced by 50%, and the productivity of the CHO#247 was doubled when compared with a control untreated with sodium butyrate (See FIG. 11). On the other hand, the cell growth rate of the F2N78_Ig treated with sodium butyrate was increased by up to 2 times, and the productivity of the F2N78_Ig was increased by 4 to 5 times when compared with a control untreated with sodium butyrate (See FIG. 12). As shown in FIG. 12, the antibody production growth rate of F2N78 was higher than that of the CHO cell line. This indicates that anti-apoptotic effects of the F2N78 cell line by sodium butyrate more significantly influence the increase in the antibody productivity.

Discussion

While EBV genomes are generally in an episomal phase in an EBV life cycle to produce virus particles, the Namalwa cell includes two copies of EBV genomes inserted into its chromosomes (Henderson et al., 1983, PNAS USA 80: 1987-1991 and Rose et al., 2002, J. Clin. Microbiol. 40:2533-2544). Such an exceptional form of the EBV genome inserted into chromosomes provides two beneficial properties to a host cell for producing recombinant proteins. First, there is no chance to produce a virus from the EBV genome inserted into the chromosome. Second, while EBNA1 proteins in a latent stage and initial genes such as BALF1 are continuously expressed, extinction of the expression of BHRF1 is observed. In particular, the extinction of BHRF1, which is one of the two viral bcl-2-related genes, is an unexpected result indicating anti-apoptotic growth of the F2N78 cell. In addition, due to the continuous expression of the EBNA1 gene, an oriP expression vector without the EBNA1 gene may be used. Furthermore, the expressions of GnTIII and α(2,6)ST offer benefits as human cells. Due to the extinction of the expressions of Ig-mu chain and Ig-kappa chain, the human host cell according to the present invention is efficiently used to produce a recombinant monoclonal antibody.

Since the decrease in mortality of the cells and the increase in cell growth period indicate the increase in the productivity of protein of interest, the anti-apoptotic cell growth is very important to increase production of recombinant proteins. These benefits were identified in the experiments of the culture of the F2N78 cell with treatment by sodium butyrate. If desired, sodium butyrate may be used to improve productivity of therapeutic proteins by the F2N78 cell.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A cell generated from fusion of a cell of human embryonic kidney origin and a cell of human B-cell origin, wherein the cell of human embryonic kidney origin is a 293 cell, and wherein the cell of human B-cell origin is a Namalwa cell that has an Epstein-Barr virus (EBV) genome inserted into its chromosomes,
   wherein the generated cell
   i) constitutively expresses EBNA1 proteins;
   ii) does not express IgM proteins;
   iii) continuously generates glycosylation profiles similar to those of humans; and
   iv) expresses BALF1, but does not express BHRF1,
   wherein the growth of the generated cell is not inhibited when sodium butyrate is added to a culture medium for the generated cell.

2. The cell of claim 1, wherein the cell is F2N78 deposited under KCTC Accession Number: KCTC 11309BP.

3. The cell of claim 1 genetically engineered to produce a recombinant protein.

4. The cell of claim 3, wherein the recombinant protein is a monoclonal antibody.

5. The cell of claim 3, wherein the recombinant protein is a therapeutic protein other than a monoclonal antibody.

* * * * *